US007824430B2

(12) United States Patent
Allard et al.

(10) Patent No.: US 7,824,430 B2
(45) Date of Patent: Nov. 2, 2010

(54) METHODS AND DEVICES FOR TREATING A MULTI-LEVEL SPINAL DEFORMITY

(75) Inventors: Randall Noel Allard, Germantown, TN (US); Mark David Waugh, Germantown, TN (US); Larry Thomas McBride, Jr., Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 931 days.

(21) Appl. No.: 11/608,334

(22) Filed: Dec. 8, 2006

(65) Prior Publication Data

US 2008/0140133 A1 Jun. 12, 2008

(51) Int. Cl.
*A61B 17/88* (2006.01)

(52) U.S. Cl. ...................................................... 606/279

(58) Field of Classification Search ......... 606/246–279, 606/53, 60, 61, 103
See application file for complete search history.

(56) References Cited

U.S. PATENT DOCUMENTS 6,551,320 B2 * 4/2003 Lieberman .................. 606/263
7,125,410 B2 10/2006 Freudiger
2005/0177156 A1 8/2005 Timm et al.
2005/0277922 A1 12/2005 Trieu et al.
2005/0277932 A1 12/2005 Farris
2005/0277934 A1 * 12/2005 Vardiman .................... 606/61
2006/0142768 A1 6/2006 Paul
2006/0195093 A1 8/2006 Jahng
2006/0247627 A1 11/2006 Farris
2007/0129729 A1 6/2007 Petit et al.

OTHER PUBLICATIONS

Showa Ika Kohgyo Co., Ltd., "N.N.C. Rod System Natural Neutral Concept Rod." Showa Spinal Implants & Instruments. 6 pages.

* cited by examiner

*Primary Examiner*—Eduardo C Robert
*Assistant Examiner*—Summer L Kostelnik

(57) ABSTRACT

The present application discloses methods for treating a multi-level spinal deformity. The methods may include inserting a tether in a minimally-invasive manner through an entrance incision. The tether is moved along the spine and positioned to reduce and/or eliminate the deformity. Once the tether is positioned along the spine, the tether may be secured to the vertebral members. In one embodiment, the tether includes a rigid section and a flexible section. The tether may be positioned within the spine with the rigid section extending along a first length of the spine and the flexible section extending along a second length of the spine. The different sections provide different corrective forces to the spine to reduce and/or eliminate the spinal deformity. In one embodiment, the rigid section extends along an apex of the spinal deformity.

23 Claims, 8 Drawing Sheets

90
80
20
80
90
80
10
95
95
30
80
20
95

METHODS AND DEVICES FOR TREATING A MULTI-LEVEL SPINAL DEFORMITY

BACKGROUND

The present application is directed to methods and devices for treating a multi-level spinal deformity and, more specifically, to a minimally-invasive method of inserting a tether into a patient.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve.

Various deformities may affect the normal alignment and curvature of the vertebral members. Scoliosis is one example of a deformity of the spine in the coronal plane, in the form of an abnormal curvature. While a normal spine presents essentially a straight line in the coronal plane, a scoliotic spine can present various lateral curvatures in the coronal plane. The types of scoliotic deformities include thoracic, thoracolumbar, lumbar or can constitute a double curve in both the thoracic and lumbar regions. Schuermann's kyphosis is another example of a spinal deformity that affects the normal alignment of the vertebral members.

Tethers may be attached to the vertebral members to reduce and/or eliminate the deformity. However, it is often difficult to insert the tether into the patient without cutting tissue and/or muscle.

SUMMARY

The present application is directed to methods of inserting a tether into a body in a minimally-invasive manner. The methods may include creating an entrance incision for percutaneous insertion. A first end of the tether is moved into the entrance and the leads the remainder of the tether into the body. The tether may be moved along one or more fasteners that are attached to and extend outward from one or more vertebral members. Once the tether is positioned along the spine, the tether may be secured to the vertebral members.

In one embodiment, the tether includes a rigid section and a flexible section. The extent of the rigidity and flexibility may vary depending upon the context of use. The tether may be positioned within the spine with the rigid section extending along a first length of the spine and the flexible section extending along a second length of the spine. The different sections provide different corrective forces to the spine to reduce and/or eliminate the spinal deformity. In one embodiment, the rigid section extends along an apex of the spinal deformity.

DETAILED DESCRIPTION

Figure 1:
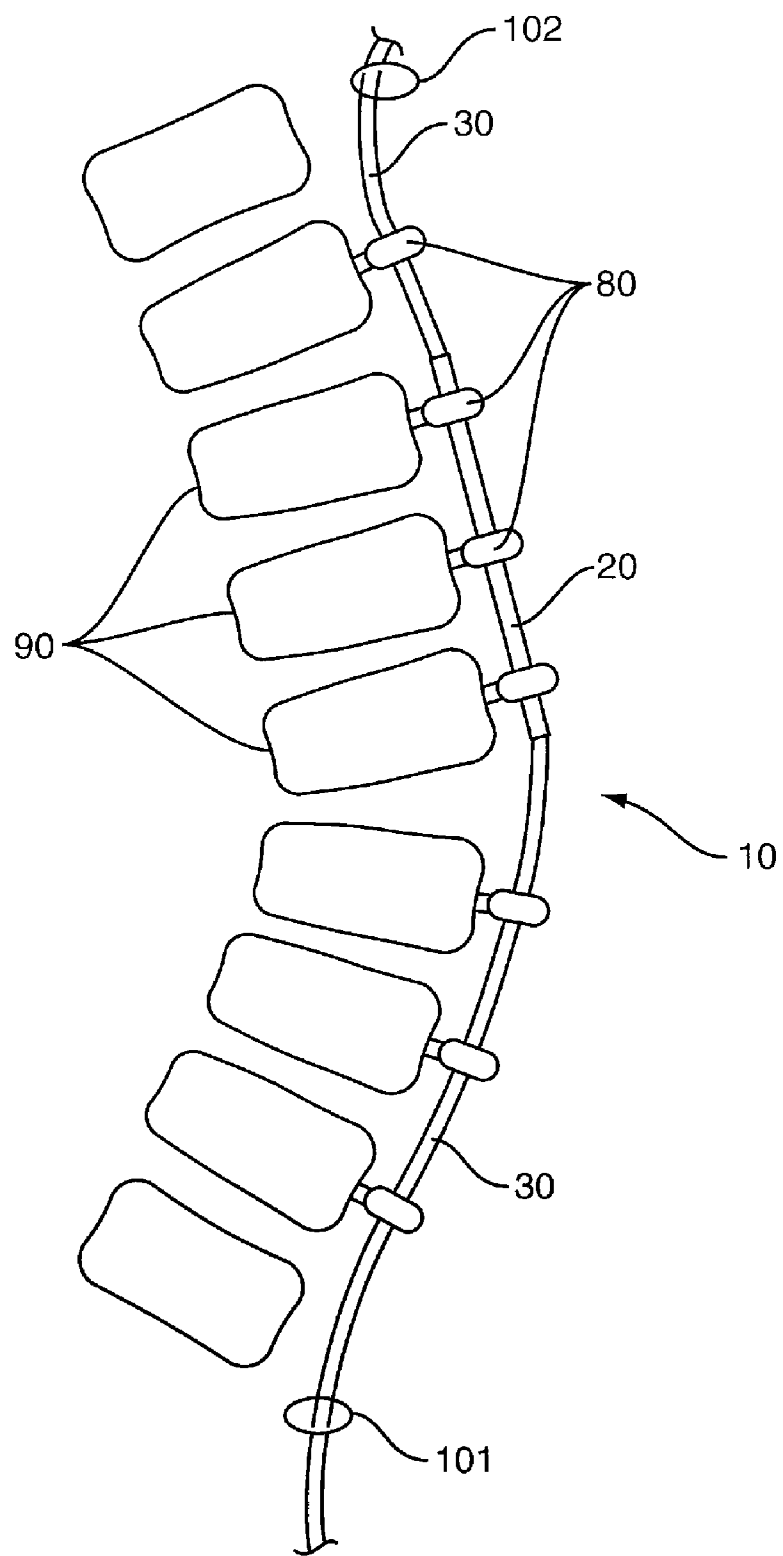
FIG. 1 is a schematic illustration of a tether attached to the spine in a percutaneous procedure according to one embodiment.

The present application is directed to minimally-invasive methods of inserting a tether into a patient and attaching the tether to the vertebral members. The methods deliver a stabilizing means with minimal excision. The tether may be substantially flexible substantially along the entire length, or may include one or more rigid sections. FIG. 1 schematically illustrates one embodiment featuring a tether 10 with an elongated shape that includes at least one rigid section 20 and at least one flexible section 30. The tether 10 is positioned along the vertebral members 90 of the spine to position the rigid and flexible sections 20, 30 at spinal levels to treat the spinal deformity. In the embodiment of FIG. 1, the rigid section 20 is positioned at an apex of the deformity with flexible sections 30 at each adjacent side. Insertion of the tether 10 may be performed percutaneously through an entrance incision 101 and an exit incision 102. The tether 10 is positioned within fasteners 80 to attach to the vertebral members 90.

Figure 2:
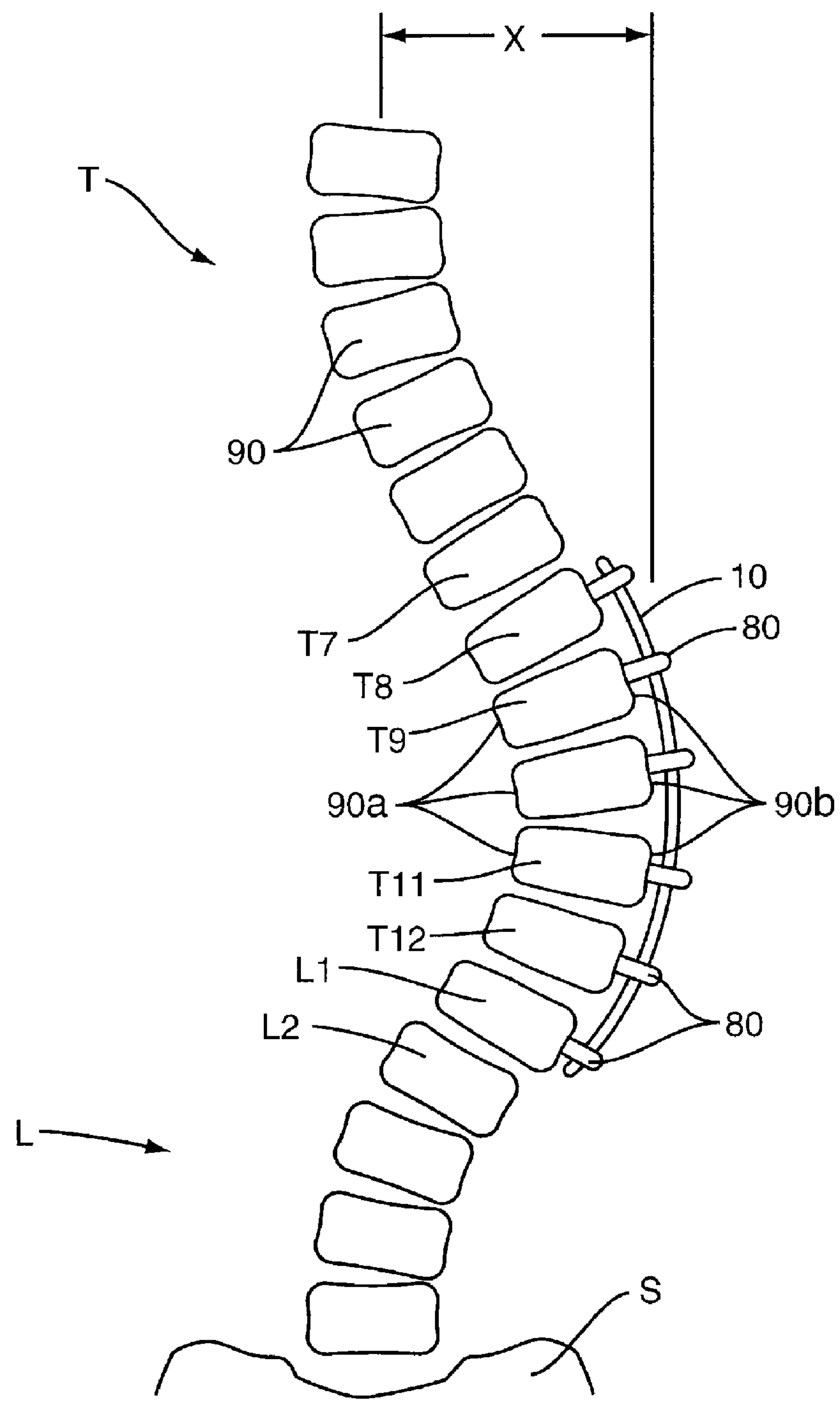
FIG. 2 is a schematic illustration of a tether attached to a deformed spine according to one embodiment.

The tether 10 may be used for treating a variety of spinal deformities, including scoliosis. FIG. 2 illustrates a patient's spine that includes a portion of the thoracic region T, the lumbar region L, and the sacrum S. This spine has a scoliotic curve with an apex of the curve being offset a distance X from its correct alignment in the coronal plane. The spine is deformed laterally so that the axes of the vertebral members 90 are displaced from the sagittal plane passing through a centerline of the patient. In the area of the lateral deformity, each of the vertebral members 90 includes a concave side 90*a* and a convex side 90*b*. In this embodiment, the tether 10 is substantially flexible along the entire length and spans between the T8 and T12 vertebral members 90. The tether 10 minimizes or arrests growth on the convex or "long" side of the spine and allows the concave or "short" side of the spine to grow and catch up with the long side. Alternatively, the tether 10 may treat the spinal deformity by simply preventing further misalignment such as curve progression.

In one embodiment, tether 10 is flexible along substantially the entire length. Embodiments include but are not limited to cables, artificial or synthetic strands, rods, plates, and springs. In one embodiment, tether 10 comprises an inner core with an outer sheath. The inner core and outer sheath may be made of a braided polymer such as polyester, polypropylene, or polyethylene. In one specific embodiment, the inner core and outer sheath are both made of polyethylene with the inner core being braided for strength and the outer sheath being braided for abrasion resistance. In one embodiment with the tether 10 being a strand, the strand may be manufactured from a variety of materials, including, but not limited to, conventional biocompatible implant alloys such as titanium, stainless steel, cobalt-chrome alloys, or even shape memory alloys and materials such as nickel-titanium.

Figure 3:
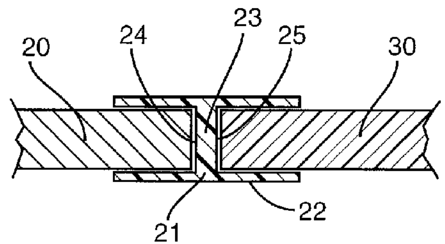
FIG. 3 is a sectional view of a section of a tether according to one embodiment.

In some embodiments, tether 10 includes one or more rigid sections 20 that are attached to one or more flexible sections 30. The sections 20, 30 may be attached together in a variety of manners. In some embodiments, a connector 21 is positioned between and connects the sections 20, 30. FIG. 3 illustrates a connector 21 with an outer wall 22 that forms a first receptacle 24 and a second receptacle 25. An interior member 23 is positioned between and separates the receptacles 24, 25. The outer wall 22 may be continuous and extend around the entire periphery of one or both receptacles 24, 25. Outer wall 22 may also include one or more apertures or extend around a limited distance of one or both receptacles 24, 25. Receptacles 24, 25 may include substantially the same configuration, or each may be different. The interior member 23 may be solid and completely segregate the receptacles 24, 25, or may include one or more openings.

Figure 4:
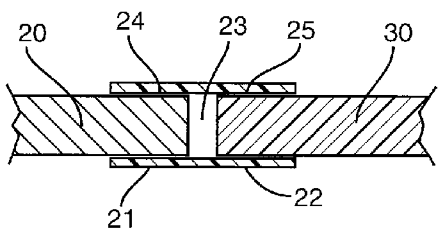
FIG. 4 is a sectional view of a section of a tether according to one embodiment.

FIG. 4 illustrates a similar connector 21 with an outer wall 22 that forms a single receptacle 24 that receives both sections 20, 30. This receptacle 24 does not include an interior member 23. The connector 21 may include a substantially cylindrical shape.

Figure 5:
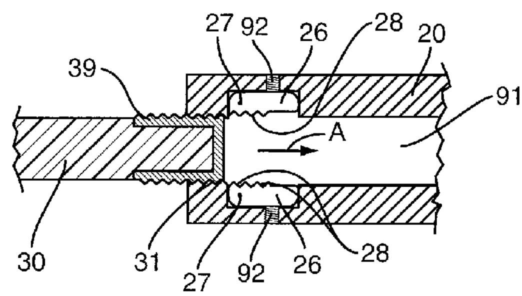
FIG. 5 is a sectional view of a section of a tether according to one embodiment.

Some embodiments feature the sections 20, 30 connecting directly together. FIG. 5 includes pivoting members 26 attached to an inner wall of the rigid section 20. Each member 26 is pivotally positioned about a pin 27 and includes teeth 28 that face inward towards an interior channel 91 of the rigid section 20. A biasing mechanism 92 may bias the members 26 towards the interior channel 91 of the rigid section 20. The flexible section 30 is sized to fit within the interior channel 91 of the rigid section 20. Flexible section 30 includes outwardly-facing teeth 31 configured to engage with the teeth 28 on the pivoting members 26. Flexible section 30 includes a width to fit within the interior channel 91 and move the pivoting members 26 outward against the force of the biasing members 92. The biasing members 92 apply an inward force to engage the teeth 28 of the rigid section 20 with the teeth 31 of the flexible section 30. The teeth 28, 31 are configured for the flexible section 30 to slide inward into the interior channel 91 of the rigid section 20 as illustrated by arrow A. Teeth 31 slide across teeth 28 during insertion and shaped to engage together and prevent movement in the opposite direction. In one embodiment, a cap 39 is attached to the end of the flexible section 30. Cap 39 includes the teeth 31 that engage with the teeth 28 on the pivoting member 26. The embodiment of FIG. 5 illustrates a pair of pivoting members 26. In another embodiment, a single pivoting member 26 may be positioned to engage the flexible section 30.

Figure 6A:
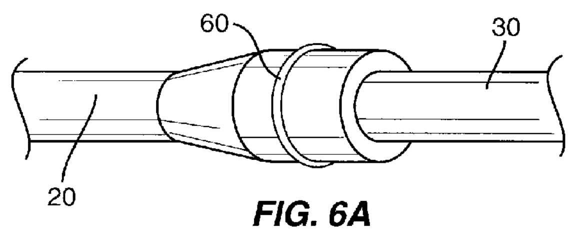
FIG. 6A is a perspective view of a section of a tether according to one embodiment.
Figure 6B:
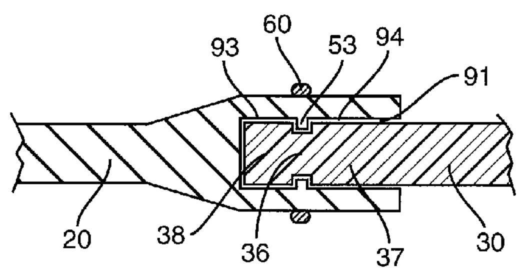
FIG. 6B is a sectional view of the tether of FIG. 6A.

FIGS. 6A and 6B illustrate another embodiment with a direct connection between the sections 20, 30. Rigid section 20 includes an enlarged end with an interior channel 91. Channel 91 includes a first interior section 93 and a second interior section 94. An extension 53 extends from the inner walls of the rigid section 20 to form a narrow opening that extends between the interior sections 93, 94. The flexible section 30 includes a neck 36 that leads to a head 38. The head 38 is sized to fit within the first interior section 93 with the neck 36 positioned at the extension 53. A clamp ring 60 is attached to the exterior of the rigid section 20. Clamp ring 60 applies a compressive force to clamp the extension 53 onto the neck 36 and maintain attachment of the sections 20, 30.

Figure 7:
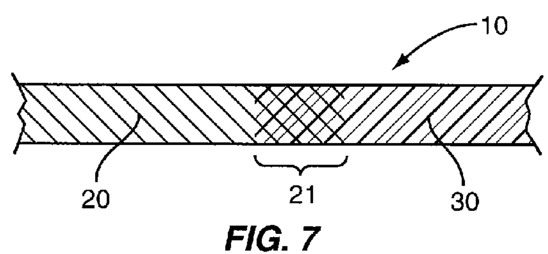
FIG. 7 is a sectional view of a section of a tether according to one embodiment.

In some embodiments, tether 10 is a single member including sections with different physical properties. FIG. 7 illustrates an embodiment with the tether 10 constructed of a rigid section 20 and a flexible section 30. An intermediate section 21 is positioned between and transitions from the rigid section 20 to the flexible section 30. In one embodiment, the sections 20, 30 are substantially the same materials with the different physical characteristics a result of the manufacturing process. In another embodiment, the sections 20, 30 include different shapes and/or sizes to cause the different physical characteristics. By way of example, the rigid section 20 includes a larger cross-sectional area than the flexible section 30.

Several methods of attaching together different elongated sections are disclosed in U.S. patent application Ser. No. 11/156,739 filed on Jun. 20, 2005 and entitled "Multi-Level Multi-Function Spinal Stabilization Systems and Methods" which is herein incorporated by reference.

The rigid section 20 includes a higher rigidity than the flexible section 30. In one embodiment, rigid section 20 includes a substantial strength to prevent bending, even during vertebral motion such as flexion, extension, and lateral bending. In one embodiment, rigid section 20 bends during vertebral motion. The rigid section 20 may be substantially straight, or may be curved to conform to the dimensions and shape of the vertebral members 90. The rigid section 20 may be constructed from a variety of different materials such as stainless steels, cobalt-chrome, titanium, and shape memory alloys. Non-metallic materials, including polymers made from materials such as PEEK and UHMWPE, are also contemplated.

Flexible section 30 includes a higher flexibility than the rigid section 20. Flexible section 30 may include a variety of different flexible materials including but not limited to cables, artificial or synthetic strands, rods, plates, and springs.

Figure 8:
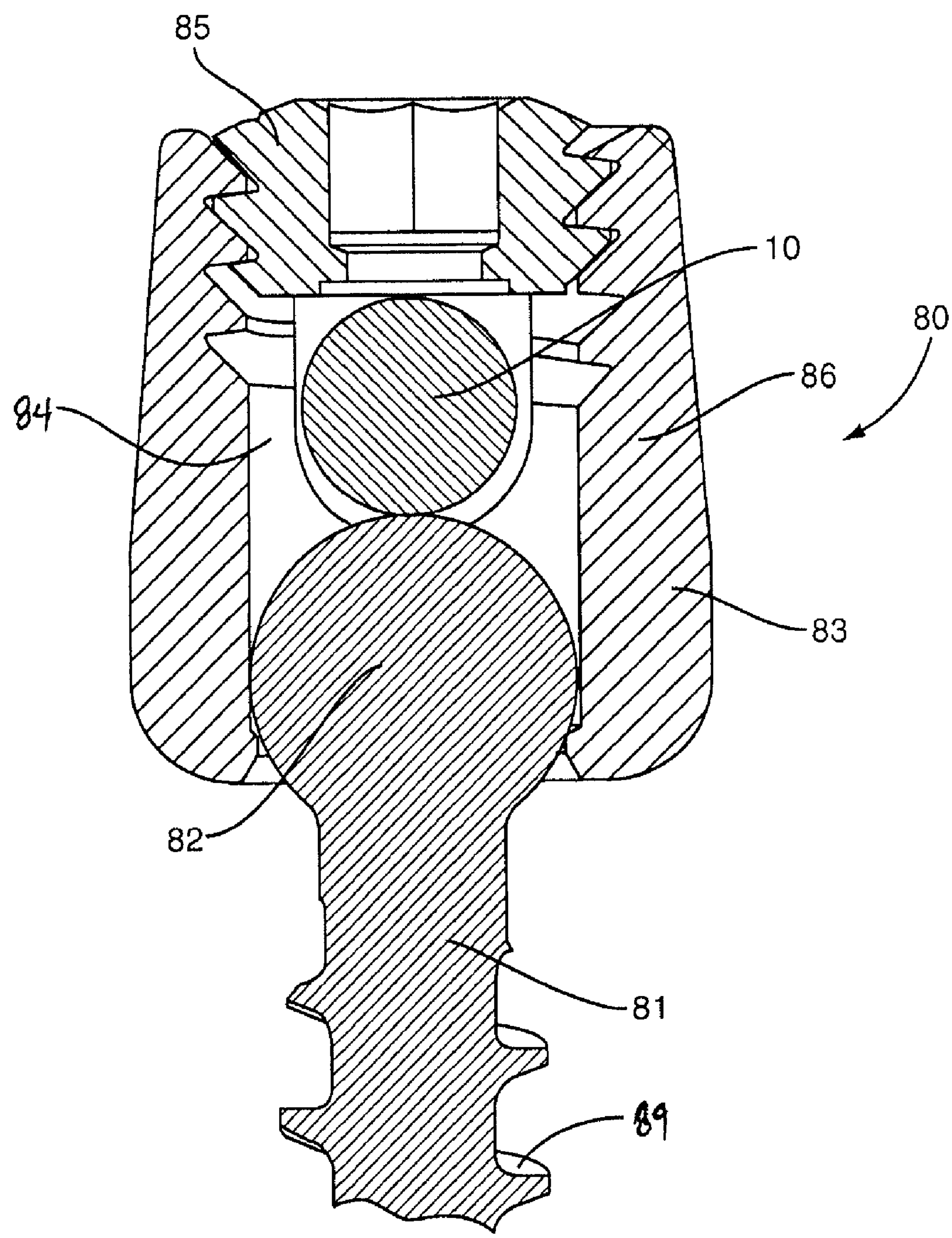
FIG. 8 is a sectional view of a tether within a fastener according to one embodiment.

Various anchors 80 may be used to connect the tether 10 to the vertebral members 90. FIG. 8 illustrates one embodiment of a multi-axial anchor 80 that includes a screw with a shaft 81 with a thread 89 that mounts to the vertebral member 90 and a substantially spherical head 82. A saddle 83 is movably mounted to the head 82 and includes opposing arms 86 that form an interior space 84 sized to receive the tether 10. A set screw 85 is threaded to the arms 86 to capture the tether 10 within the interior space 84. The saddle 83 is pivotally and rotatably connected to the head 82. This connection provides for multi-axial movement of the tether 10 relative to the vertebral member 90 to which the shaft 81 is attached. FIG. 8 illustrates an anchor 80 that is top-loading (i.e., the arms 86 are open towards the top opposite from the shaft 81). In another embodiment, the anchor 80 is side-loading.

Other anchors 80 may also be used for attaching the tether 10 to the vertebral members 90. In one embodiment, anchor 80 includes a fixed saddle 83 that does not move relative to the shaft 81. In another embodiment, anchor 80 is a staple that is substantially C-shaped to extend over and connect the tether 10 to the vertebral member 90.

The tether 10 is attached to the vertebral members 90 in a minimally-invasive manner. The tether 10 is fed through the skin, under the muscle, around the nerves, and over the vertebral members 90. Previous methods have disturbed the soft tissue and bone resulting in the body protecting the affected area by producing scar tissue and eventually fusing.

Figure 9:
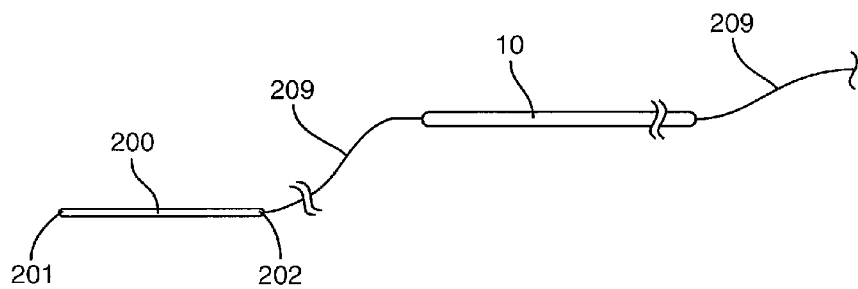
FIG. 9 is a side view of a guide attached to a tether according to one embodiment.

FIG. 9 illustrates the tether 10 attached to a guide 200 for inserting and positioning the tether 10 in the body. Guide 200 includes an elongated shape with a leading end 201 and a trailing end 202. The guide 200 may be substantially straight or may be curved. The leading end 201 may include a sharpened point to facilitate insertion into and through the body. The trailing end 202 may include an eyelet or other like opening to connect with the tether 10. A connector 209 may extend from the tether 10 to connect with the trailing end 202. The connector 209 may be tied or otherwise attached to the trailing end 202.

Figure 10A:
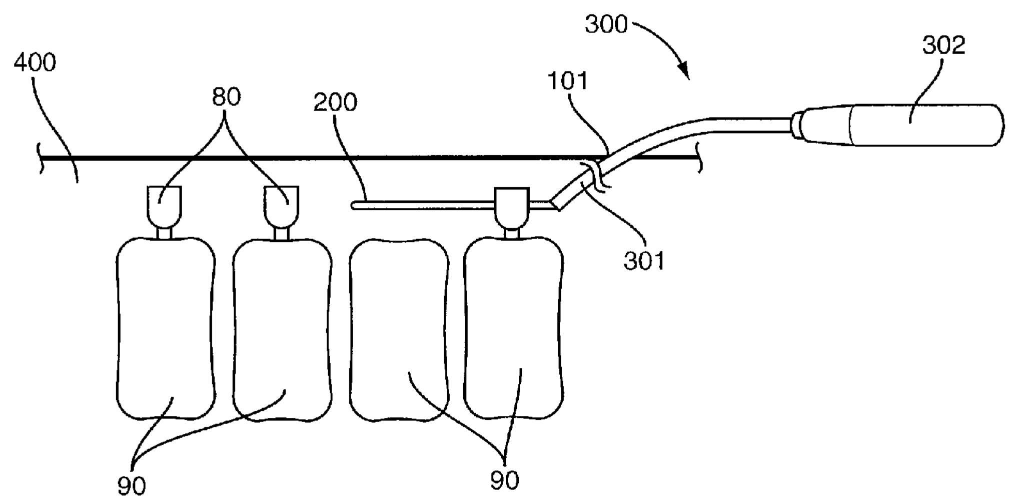
FIG. 10A is a side schematic view of a tether being inserted into the body with an insertion tool according to one embodiment.
Figure 10B:
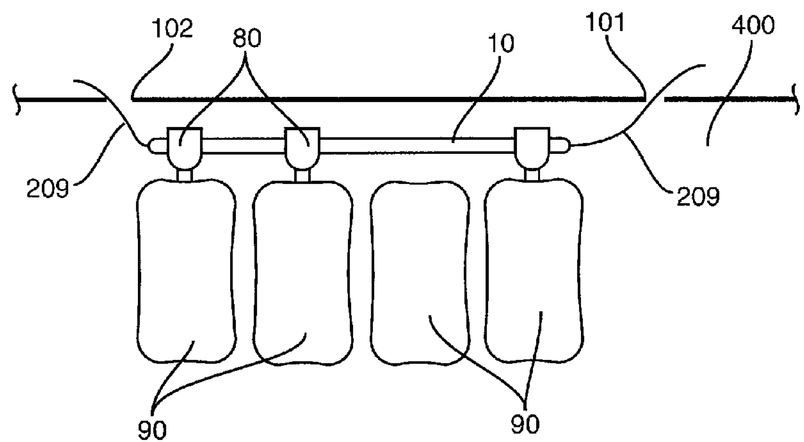
FIG. 10B is a side schematic view of a tether inserted within the body according to one embodiment.

FIGS. 10A and 10B schematically illustrate insertion of the tether 10 into the body 400. Tether 10 is attached to an insertion tool 300 for insertion and positioning with the body 400. Tool 300 includes a handle 302 for grasping by the surgeon, and an elongated neck 301 sized to receive the guide 200 and fit within the entrance 101. The guide 200 is attached to the tool 300 such that the leading end 201 extends outward beyond the end of the neck 301. The remainder of the guide 200 and the tether 10 are positioned within a channel that extends along the neck 301 to provide for reduced overall size of the tool for minimal intrusion into the body 400.

After the tether 10 is attached, the tool 300 is then manipulated by the surgeon to move the guide 200 and attached tether 10 through the fasteners 80. In one embodiment, the leading end 201 followed by the remainder of the guide 200 and the leading section of the tether 10 move through the saddle of the fastener 80. In one embodiment, the tool 300 is further inserted into the body 400 such that the leading end 201 is moved through the exit 102 and out of the body. The leading connector 209 is grasped by the surgeon at the exit 102 and the insertion tool 300 is disconnected from the tether 10 and removed from the body through the entrance 101.

FIG. 10B illustrates the tether 10 removed from the tool 300 and positioned within the body 400. Leading and trailing connectors 209 extend through the exit and entrance 102, 101. The connectors 209 may be manipulated by the surgeon to position the tether 10 along vertebral members 90 of the spine. Manipulating the position of the tether 10 may include positioning the rigid section 20 and flexible section 30 relative to the spinal deformity. After positioning, the tether 10 is attached to each fastener 80 with a set screw 85 (see FIG. 8). After the tether 10 is positioned within the body 400, the connectors 209 may be removed from the tether 10.

In a similar embodiment, tether 10 includes a leading rigid section 20 and a flexible section 30. The rigid section 20 is attached directly to the insertion tool 300 and inserted into the body 400. In another embodiment, the tether 10 is inserted through the entrance 101 and positioned within the body 400 by the insertion tool 300. The insertion tool 300 is sized to move the tether 10 within the body 400 and does not require an exit incision 102.

Figure 11:
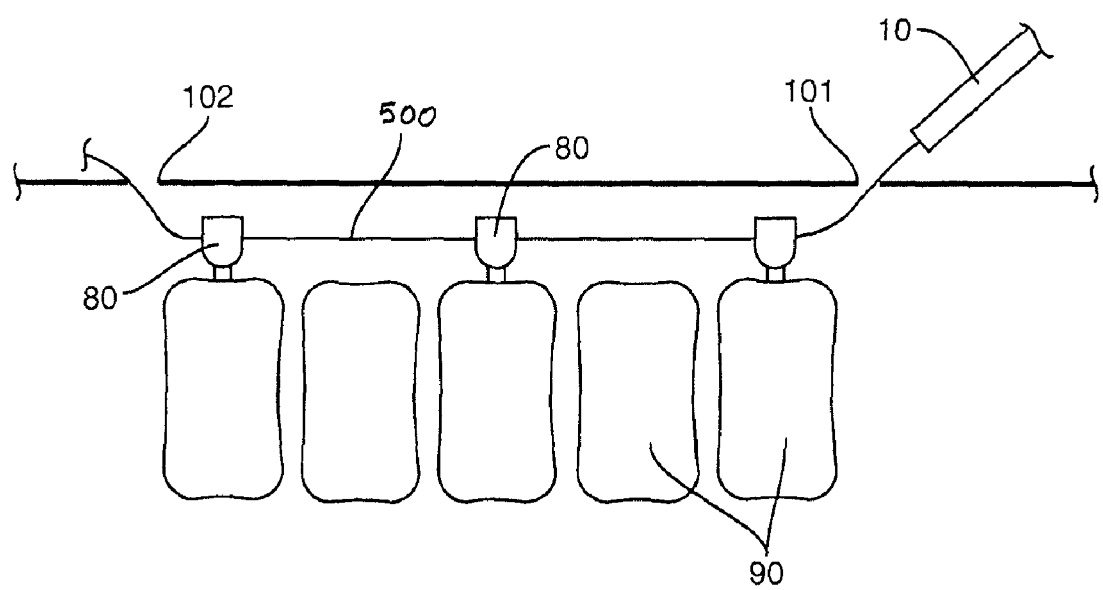
FIG. 11 is a side schematic view of a tether attached to a guide member according to one embodiment.

FIG. 11 illustrates another method of insertion that includes a guide member 500 that is previously inserted within the body 400 prior to insertion of the tether 10. Guide member 500 extends from the entrance 101 to the exit 102 and through the fasteners 80. The tether 10 is initially attached to the guide member 500. The attachment may occur outside of the body 400, or within the body 400. After attachment, the tether 10 is moved along the guide member 500 and through the fasteners 80. After the tether 10 is positioned properly within the body 400, the guide member 500 may be removed.

Figure 12:
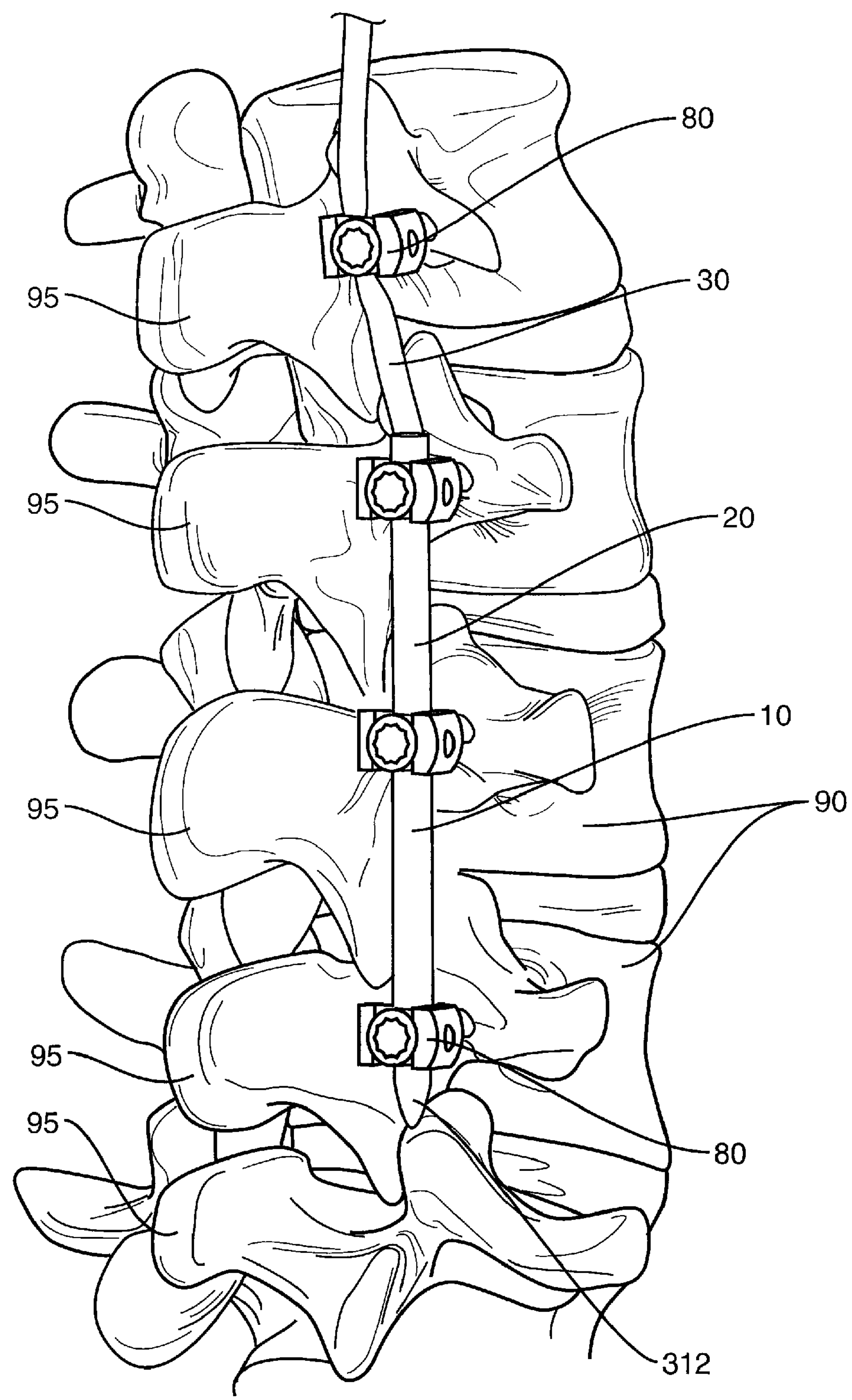
FIG. 12 is a partial perspective view of a tether attached to vertebral members according to one embodiment.

FIG. 12 illustrates another embodiment with the tether 10 including a leading rigid section 20 and a trailing flexible section 30. The rigid section 20 includes a pointed leading end 312 to facilitate insertion into the entrance 101 and through the body 400.

Figure 13:
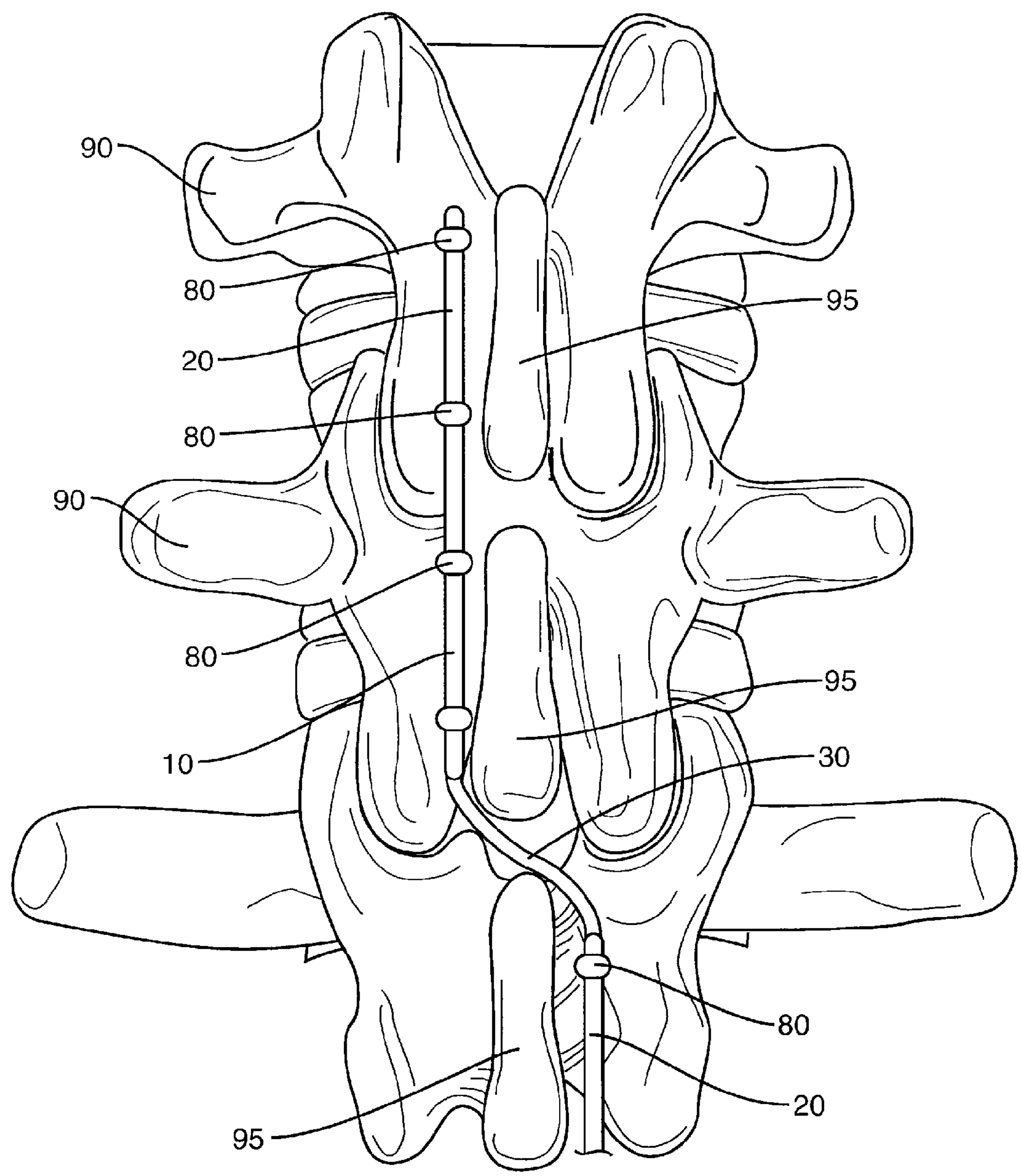
FIG. 13 is a partial perspective view of a tether attached to vertebral members according to one embodiment.

The embodiment of FIG. 12 includes the tether 10 extending along one side of the spinous processes 95. FIG. 13 includes another embodiment with the tether 10 extending along both sides of the spinous processes 95. In this embodiment, a flexible section 30 extends through an interspinous space and connects with rigid sections 20 that extend along the spinous processes 95. In one embodiment, the tether 10 of FIG. 13 is inserted through a posterior approach. In one embodiment that extends along both sides of the spinous processes 95, the rigid section 20 is positioned on the concave side of the spinous processes 95 and flexible section 30 passes through the interspinous space and extends along the convex side of the spinous processes 95.

In one embodiment, a rigid section 20 is positioned at the apex of the spinal deformity. In another embodiment, a flexible section 30 is positioned at the apex of the spinal deformity.

In the various embodiments, the tether 10 may be inserted into the body 400 in either a cranial direction or a caudal direction.

The tether 10 may include one or more rigid sections 20 and one or more flexible sections 30. The lengths of each of the sections 20, 30 may be the same or may be different depending upon the context of use.

One embodiment includes accessing the spine from a postero-lateral, antero-lateral and lateral approaches to the spine. In another embodiment, the tether 10 is inserted with a posterior approach.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A method of treating a multi-level spinal deformity comprising:

percutaneously inserting a first end of a tether through an entrance incision into a body, the tether including an elongated rigid section and an elongated flexible section connected to an end of the rigid section;

threading the tether through a plurality of fasteners attached to vertebral members;

moving the first end of the tether through an exit incision and out of the body;

positioning the rigid section of the tether at an apex of the spinal deformity and the flexible section on a first longitudinal side of the apex; and securing each of the rigid section and the flexible section to the vertebral members with at least one of the plurality of fasteners.

2. The method of claim 1, wherein the step of threading the tether through the plurality of fasteners attached to vertebral members comprises inserting the tether through a saddle of each of the plurality of fasteners.

3. The method of claim 2, wherein the step of securing the tether to each of the plurality of fasteners comprises capturing the tether with a set screw within the saddle of each of the plurality of fasteners.

4. The method of claim 1, further comprising attaching a guide to a first end of the tether and leading the tether through the fasteners with the guide.

5. The method of claim 1, wherein the step of threading the tether through the plurality of fasteners comprises moving the tether along a guide member.

6. The method of claim 1, further comprising removing a section of the tether that extends beyond the exit incision after the section moves through the exit incision and out of the body.

7. The method of claim 1, further comprising positioning a first section of the tether along a first side of spinous processes and a second section on a second side of the spinous processes.

8. The method of claim 7, further comprising positioning the flexible section of the tether between the first and second sections through an interspinous space.

9. A method of treating a multi-level spinal deformity comprising:

percutaneously inserting a rigid section of a tether through an entrance incision in the body;

moving the rigid section through a first fastener attached to a first vertebral member;

after the rigid section moves through the first fastener, moving a flexible section of the tether attached to the rigid section into the first fastener, the flexible section being attached to the rigid section in an end-to-end orientation with ends of the flexible and rigid sections facing towards each other, being aligned with each other, and being in a non-overlapping orientation;

moving the rigid section through a second fastener attached to a second vertebral member;

positioning the rigid section along a first side of spinous processes, positioning the flexible section within an interspinous space, and positioning a third section along a second side of the spinous processes;

securing the rigid section to the second fastener; and securing the flexible section to the first fastener.

10. The method of claim 9, further comprising positioning a connection between the rigid section and the flexible section between the first and second fasteners.

11. The method of claim 9, further comprising positioning the rigid section at an apex of the spinal deformity.

12. The method of claim 9, wherein the step of percutaneously inserting the rigid section of the tether through the entrance incision in the body comprises initially inserting a pointed leading end of the rigid section into the entrance.

13. The method of claim 9, further comprising moving the rigid section and the flexible section along a guide member within the body.

14. The method of claim 9, further comprising inserting a leading member into the entrance incision prior to inserting the rigid section through the entrance.

15. The method of claim 14, further comprising moving the leading member out of an exit incision while the rigid section is within the second fastener.

16. The method of claim 9, further comprising attaching the rigid section to an insertion tool and manipulating the insertion tool and inserting the rigid section into the entrance incision.

17. A method of treating a multi-level spinal deformity comprising:

percutaneously inserting a tether through an entrance incision, the tether including an intermediate flexible section with opposing first and second ends, a first rigid section attached to the first end, and a second rigid section attached to the second end;

moving the tether through a plurality of fasteners each attached to one a plurality of vertebral members;

positioning the first rigid section of the tether along a first section of the plurality of vertebral members on a first lateral side of spinous processes;

positioning the second rigid section of the tether along a second section of the plurality of vertebral members on a second lateral side of the spinous processes;

positioning the flexible section of the tether through an interspinous space between the first and second sections; and securing the tether to the plurality of vertebral members.

18. The method of claim 17, wherein the step of percutaneously inserting the tether through the entrance incision comprises inserted a pointed end of the rigid section initially into the entrance.

19. The method of claim 17, wherein the step of percutaneously inserting the tether through the entrance incision comprises attaching a guide to the tether and inserting the guide into the entrance incision prior to inserting the tether into the entrance incision.

20. The method of claim 17, further comprising moving the tether along a guide member and positioning the tether relative to the plurality of vertebral members.

21. The method of claim 17, further comprising positioning a pointed end of the rigid section within the patient.

22. A method of treating a multi-level spinal deformity comprising:

inserting a rigid first end of a tether through an entrance incision;

moving the rigid first end of the tether along a plurality of vertebral members;

positioning a rigid section of the tether along a first length of the vertebral members;

positioning a flexible section of the tether along a second length of the vertebral members; and positioning the rigid section along a first lateral side of the vertebral members and positioning the flexible section along a second lateral side of the vertebral members;

securing the rigid section and the flexible section to the vertebral members with a first plurality of anchors connecting the flexible section along the first length of the vertebral members and a second plurality of anchors connecting the rigid section along the second length of the vertebral members.

23. The method of claim 22, wherein positioning the rigid and flexible sections of the tether comprises positioning connectors that extend from ends of the tether within the entrance incision and an exit incision and manipulating the connectors.

* * * * *